(12) United States Patent
Kyser et al.

(10) Patent No.: US 10,057,337 B2
(45) Date of Patent: Aug. 21, 2018

(54) VIDEO LOAD BALANCING SYSTEM FOR A PEER-TO-PEER SERVER NETWORK

(71) Applicant: AvaSure, LLC, Belmont, MI (US)

(72) Inventors: Ryan Kyser, Hudsonville, MI (US);
Brian Meinke, Rockford, MI (US);
Brian John Ensink, Hudsonville, MI (US)

(73) Assignee: AvaSure, LLC, Belmont, MI (US)

( * ) Notice: Subject to any disclaimer, the term of this patent is extended or adjusted under 35 U.S.C. 154(b) by 176 days.

(21) Appl. No.: 15/241,355

(22) Filed: Aug. 19, 2016

(65) Prior Publication Data
US 2018/0054476 A1 Feb. 22, 2018

(51) Int. Cl.
*H04L 29/08* (2006.01)
*H04L 29/06* (2006.01)
*A61B 5/00* (2006.01)

(52) U.S. Cl.
CPC ........ *H04L 67/1002* (2013.01); *A61B 5/0013* (2013.01); *A61B 5/0022* (2013.01);
(Continued)

(58) Field of Classification Search
CPC ... A61B 5/0013; A61B 5/0022; A61B 5/0077; H04L 65/4069; H04L 65/80; H04L 67/1002; H04L 67/1076; H04L 67/12
See application file for complete search history.

(56) References Cited

U.S. PATENT DOCUMENTS 7,733,808 B2 6/2010 Hu et al.
7,792,915 B2 9/2010 Berkey et al.
(Continued)

FOREIGN PATENT DOCUMENTS

| CN | 103354545 | 10/2013 |
|---|---|---|
| EP | 1926276 | 5/2008 |

(Continued)

OTHER PUBLICATIONS

Ayyasamy S. et al., "A Cluster Based Replication Architecture for Load Balancing in Peer-to-Peer Content Distribution," International Journal of Computer Networks & Communications, Sep. 2010, vol. 2, No. 5, pp. 158-172.

(Continued)

*Primary Examiner* — Alina A Boutah
(74) *Attorney, Agent, or Firm* — Price Heneveld LLP

(57) ABSTRACT

A live-feed video balancing system includes a peer-to-peer server network wherein each server communicates with the remaining servers of the peer-to-peer server network and each monitors corresponding performance criteria of a dedicated server of the peer-to-peer server network to define a hosting capacity for the dedicated server. The hosting capacity is communicated to the remaining servers and the servers cooperatively assess the corresponding hosting capacities from the monitoring servers to determine a potential hosting server having a first hosting capacity and the remaining servers have a range of second hosting capacities. The potential hosting server, in response to a hosting request, is placed in communication with an image capturing device that delivers the live video feed. The hosting server places the image capturing device in selective communication with the potential hosting server to deliver the live video feed to the customer terminal to define an active hosting server.

20 Claims, 15 Drawing Sheets

(52) U.S. Cl.
CPC ........ *A61B 5/0077* (2013.01); *H04L 65/4069* (2013.01); *H04L 65/80* (2013.01); *H04L 67/1076* (2013.01); *H04L 67/12* (2013.01)

(56) References Cited

U.S. PATENT DOCUMENTS

| | | | |
|---|---|---|---|
| 7,941,482 B2 | 5/2011 | Bates et al. | |
| 7,996,546 B2 | 8/2011 | Luzzatti et al. | |
| 8,116,235 B2 | 2/2012 | Hu et al. | |
| 8,214,489 B2 | 7/2012 | Ballette et al. | |
| 8,316,146 B2 | 11/2012 | Ehn et al. | |
| 8,346,882 B2 | 1/2013 | Berkey et al. | |
| 8,477,658 B2 | 7/2013 | Tsang et al. | |
| 8,650,301 B2 | 2/2014 | Luzzatti et al. | |
| 8,726,327 B2 | 5/2014 | Miao et al. | |
| 8,769,610 B1* | 7/2014 | Giguiere | H04L 63/20 726/1 |
| 8,909,747 B2 | 12/2014 | Steiner et al. | |
| 9,094,263 B2 | 7/2015 | Cohen | |
| 9,325,786 B2 | 4/2016 | Chan et al. | |
| 9,680,926 B2* | 6/2017 | El-Beltagy | H04L 67/1046 |
| 2005/0044268 A1* | 2/2005 | Johnston-Watt | H04L 12/583 709/238 |
| 2007/0204078 A1* | 8/2007 | Boccon-Gibod | G06F 21/10 710/54 |
| 2008/0112315 A1* | 5/2008 | Hu | H04N 7/17318 370/230 |
| 2008/0133767 A1* | 6/2008 | Birrer | H04L 65/4076 709/231 |
| 2008/0158366 A1* | 7/2008 | Jung | G03B 17/20 348/207.1 |
| 2009/0113253 A1* | 4/2009 | Wang | H04L 65/1013 714/48 |
| 2009/0164615 A1 | 6/2009 | Akkanen | |
| 2010/0131620 A1 | 5/2010 | Kondamuru et al. | |
| 2011/0173265 A1 | 7/2011 | Liang et al. | |
| 2011/0219137 A1 | 9/2011 | Yang et al. | |
| 2013/0024583 A1 | 1/2013 | Kim et al. | |
| 2013/0086278 A1 | 4/2013 | Schmidt | |
| 2015/0087371 A1* | 3/2015 | Hill | G07F 17/3293 463/11 |
| 2015/0181165 A1 | 6/2015 | Iltus | |
| 2015/0222656 A1* | 8/2015 | Haugsnes | H04L 63/1441 726/23 |
| 2016/0219117 A1* | 7/2016 | Marlatt | G06F 9/5027 |
| 2016/0287166 A1* | 10/2016 | Tran | H04B 1/3827 |
| 2017/0195386 A1* | 7/2017 | Nathan | H04L 65/4084 |

FOREIGN PATENT DOCUMENTS

| | | |
|---|---|---|
| WO | 2004110024 | 12/2004 |
| WO | 2008040199 | 4/2008 |
| WO | 2008061022 | 5/2008 |
| WO | 2008074888 | 6/2008 |
| WO | 2008089686 | 7/2008 |
| WO | 2009145748 | 12/2009 |
| WO | 2011157295 | 12/2011 |
| WO | 2012115783 | 8/2012 |

OTHER PUBLICATIONS

Laing, Chao et al., "Hierarchically Clustered P2P Streaming System," Polytechnic University, Global Telecommunications Conference, 2007, 9 pages.

Soujanya, K. et al., "Structured Peer-to-Peer Systems Using Load Balancing With Imperfect Information," International Journal of Advanced Research in Computer Science and Software Engineering, Aug. 2012, vol. 2, Issue 8, pp. 263-267.

\* cited by examiner

US 10,057,337 B2

VIDEO LOAD BALANCING SYSTEM FOR A PEER-TO-PEER SERVER NETWORK

FIELD OF THE INVENTION

The present invention generally relates to a system for live streaming video via a multi-server server network, and more specifically, utilizing a peer-to-peer server network for live streaming video from an image capturing device to a customer terminal via the peer-to-peer server network.

BACKGROUND OF THE INVENTION

The use of video surveillance is implemented in many industries, including the health care industry. The monitoring of patients and health care providers can help to promote the performance of proper health care standards. Challenges involved in monitoring patients can include various health care laws that prevent the unauthorized sharing of healthcare information. Accordingly, such live video feeds must be transferred through a server without being recorded.

SUMMARY OF THE INVENTION

According to one aspect of the present invention, a live-feed video balancing system includes a plurality of servers placed in communication to define a peer-to-peer server network. Each server of the peer-to-peer server network is placed in communication with each of the remaining servers of the peer-to-peer server network. Each server of the peer-to-peer server network defines a monitoring server that monitors at least one corresponding performance criteria of a dedicated server of the peer-to-peer server network. Each monitoring server defines a corresponding hosting capacity for the dedicated server, wherein the corresponding hosting capacity is based on the at least one corresponding performance criteria. Each monitoring server communicates the corresponding hosting capacity of the dedicated server to the remaining servers such that the hosting capacity is communicated to the remaining servers at predetermined intervals. The plurality of servers of the peer-to-peer server network cooperatively assess the communicated corresponding hosting capacities from all of the monitoring servers to determine a potential hosting server. The potential hosting server has a first hosting capacity and the remaining servers have a range of second hosting capacities. The first hosting capacity is greater than any of the corresponding hosting capacities within the range of second hosting capacities. The potential hosting server, in response to a request for a live video feed from a customer terminal, is placed in communication with an image capturing device that delivers the live video feed. The hosting server is adapted to place the image capturing device in selective communication with the potential hosting server to deliver the live video feed to the customer terminal to define an active hosting server.

According to another aspect of the present invention, a method for live streaming a plurality of server-hosted video feeds includes identifying a plurality of potential customer terminals, identifying a plurality of image capturing devices, coupling a plurality of servers to define a peer-to-peer server network, wherein each server of the peer-to-peer server network is in communication with each remaining server of the peer to peer server network. A corresponding hosting capacity for each server of the plurality of servers is determined, wherein each server defines a monitoring server that operates to monitor at least one performance criteria of one corresponding monitored server within the peer-to-peer server network. Each monitoring server assigns a corresponding hosting capacity for the corresponding monitored server based upon the at least one performance criteria of the corresponding monitored server, and the corresponding hosting capacity of each corresponding monitored server of the peer-to-peer server network is communicated to each remaining server of the peer-to-peer server network. A video request is delivered from a requesting customer terminal of the plurality of potential customer terminals to the peer-to-peer server network, wherein the video request identifies a requested image capturing device of the plurality of image capturing devices that is to be placed in communication with the requesting customer terminal via a hosting server of the peer-to-peer server network. The hosting server is identified, wherein the hosting server is defined as the server having a first corresponding hosting capacity and the remaining servers are defined as having a range of second corresponding hosting capacities, wherein the first corresponding hosting capacity is greater than any of the corresponding hosting capacities within the range of second corresponding hosting capacities. The requested image capturing device is placed in communication with the hosting server and the hosting server is placed in communication with the requesting customer terminal to deliver a live video feed from the requested image capturing device to the requesting customer terminal.

According to another aspect of the present invention, a method for live streaming a plurality of server-hosted video feeds includes defining a server web defined by a plurality of self-monitoring servers, wherein each self-monitoring server of the server web is in communication with each remaining server of the server web. Each self-monitoring server monitors at least one corresponding performance criteria of the respective self-monitoring server, and wherein each self-monitoring server communicates the corresponding performance criteria to each remaining server of the server web. A potential hosting server is determined, wherein the self-monitoring servers of the server web assess each corresponding performance criteria to define a first performance criteria that corresponds to the potential hosting server, and wherein each remaining performance criteria of the remaining self-monitoring servers collectively defines a range of second performance criteria. A plurality of potential customer terminals is identified. A plurality of image capturing devices is identified. A video request from a requesting customer terminal of the plurality of potential customer terminals is delivered to the peer-to-peer server network, wherein the video request identifies a requested image capturing device of the plurality of image capturing devices that is to be placed in communication with the requesting customer terminal via a hosting server of the peer-to-peer server network. The potential hosting server is placed in communication with the requested image capturing device and the requesting customer terminal, wherein the potential hosting server defines an active hosting server that places the requested image capturing device in communication with the requesting customer terminal via the active hosting server. An updated potential hosting server is redetermined, wherein the active hosting server and the remaining self-monitoring servers of the server web communicates updated corresponding performance criteria to each other self-monitoring server of the server web to redefine an updated first corresponding performance criterial and an updated range of second corresponding performance criteria.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 1:
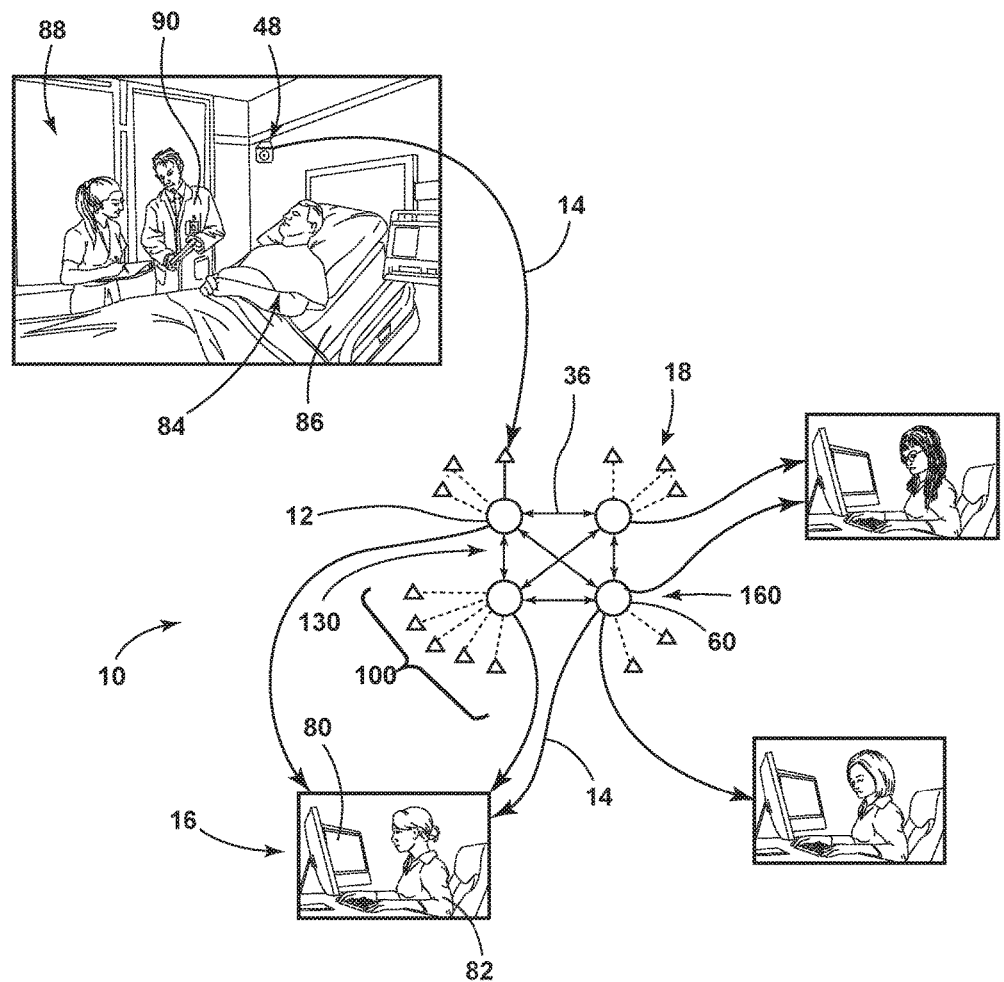
FIG. 1 is a schematic perspective view of a healthcare environment incorporating an aspect of the peer-to-peer server network for delivering a live video feed from an image capturing device to a custom terminal.
Figure 2:
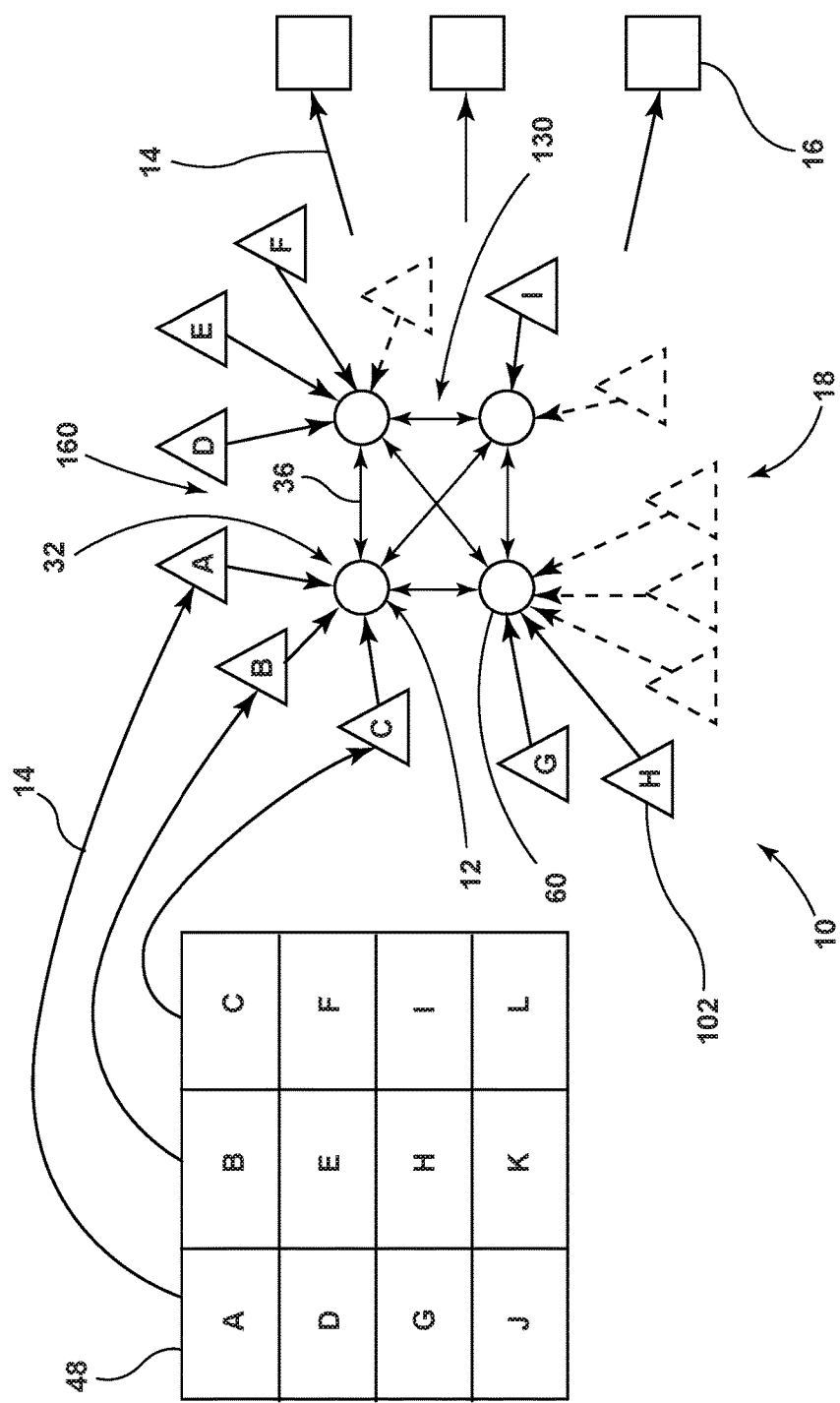
FIG. 2 is a schematic diagram illustrating an aspect of the peer-to-peer server network operating in conjunction with a plurality of image capturing devices and a plurality of customer terminals.
Figure 3:
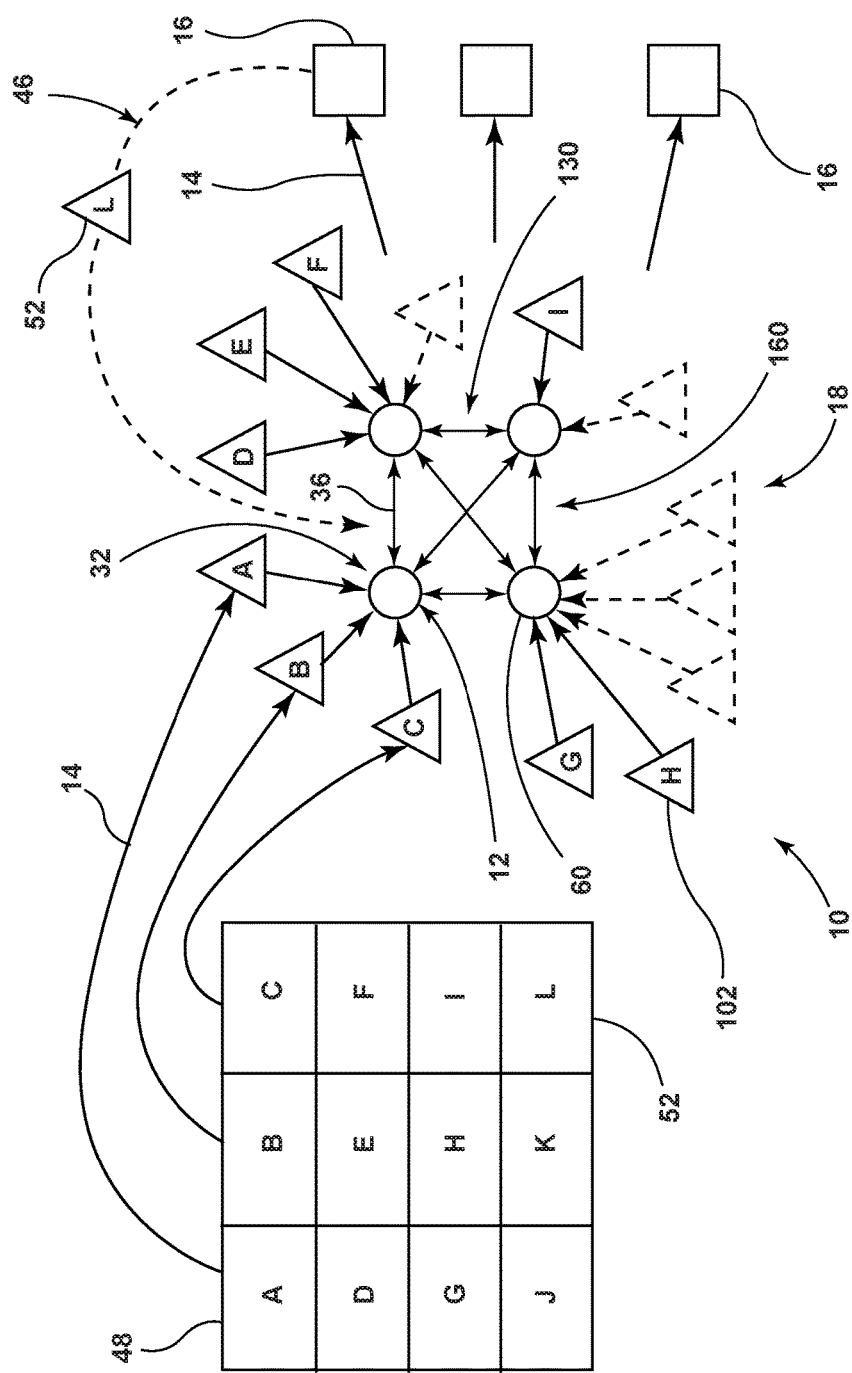
FIG. 3 is a schematic illustration exemplifying the peer-to-peer server network of FIG. 2 and showing the occurrence of a request from a customer terminal for a live video feed.
Figure 4:
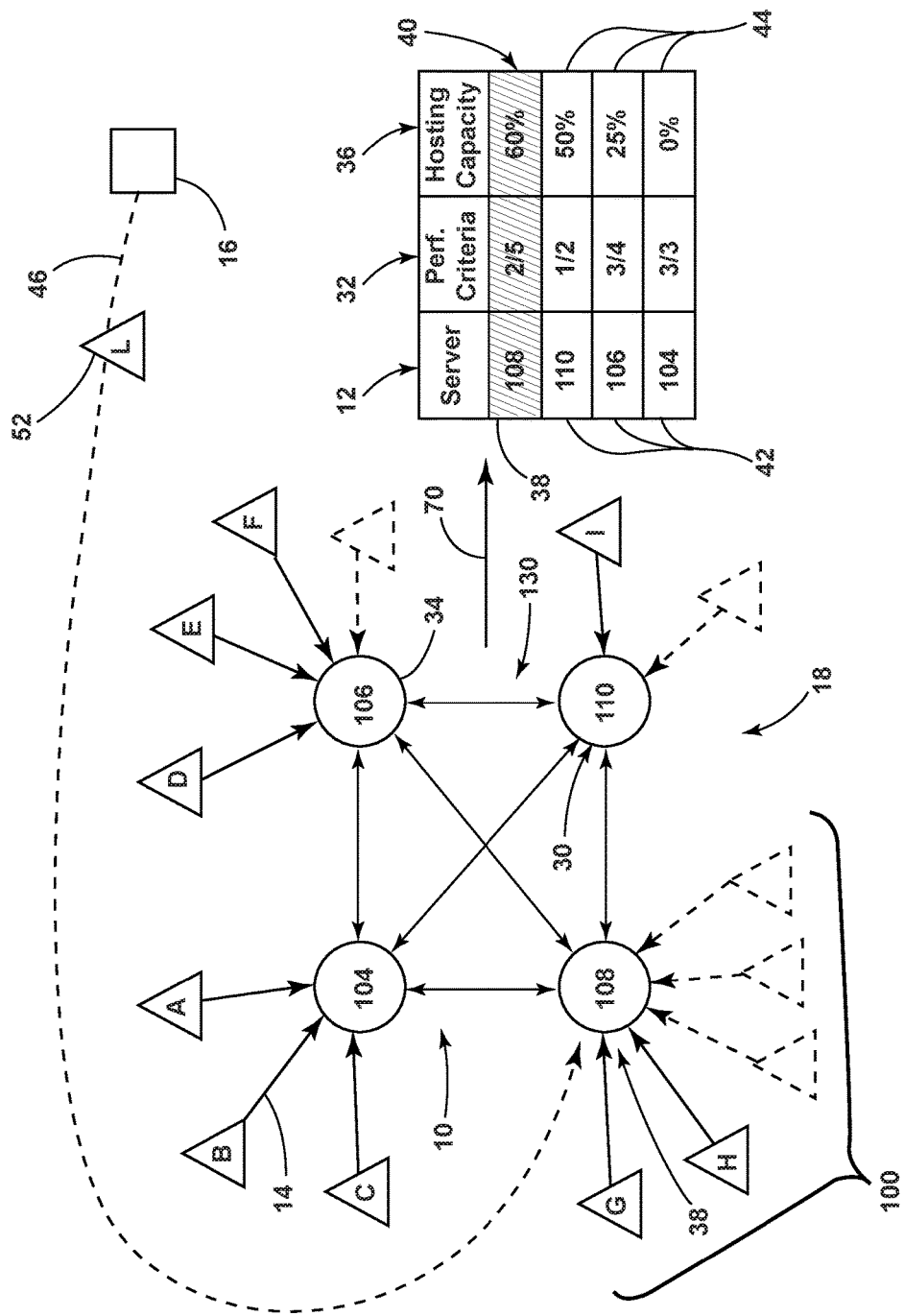
FIG. 4 is a schematic illustration exemplifying the peer-to-peer server network of FIG. 3 showing the occurrence of an assessment of the potential hosting server among the various servers of the peer-to-peer server network.
Figure 5:
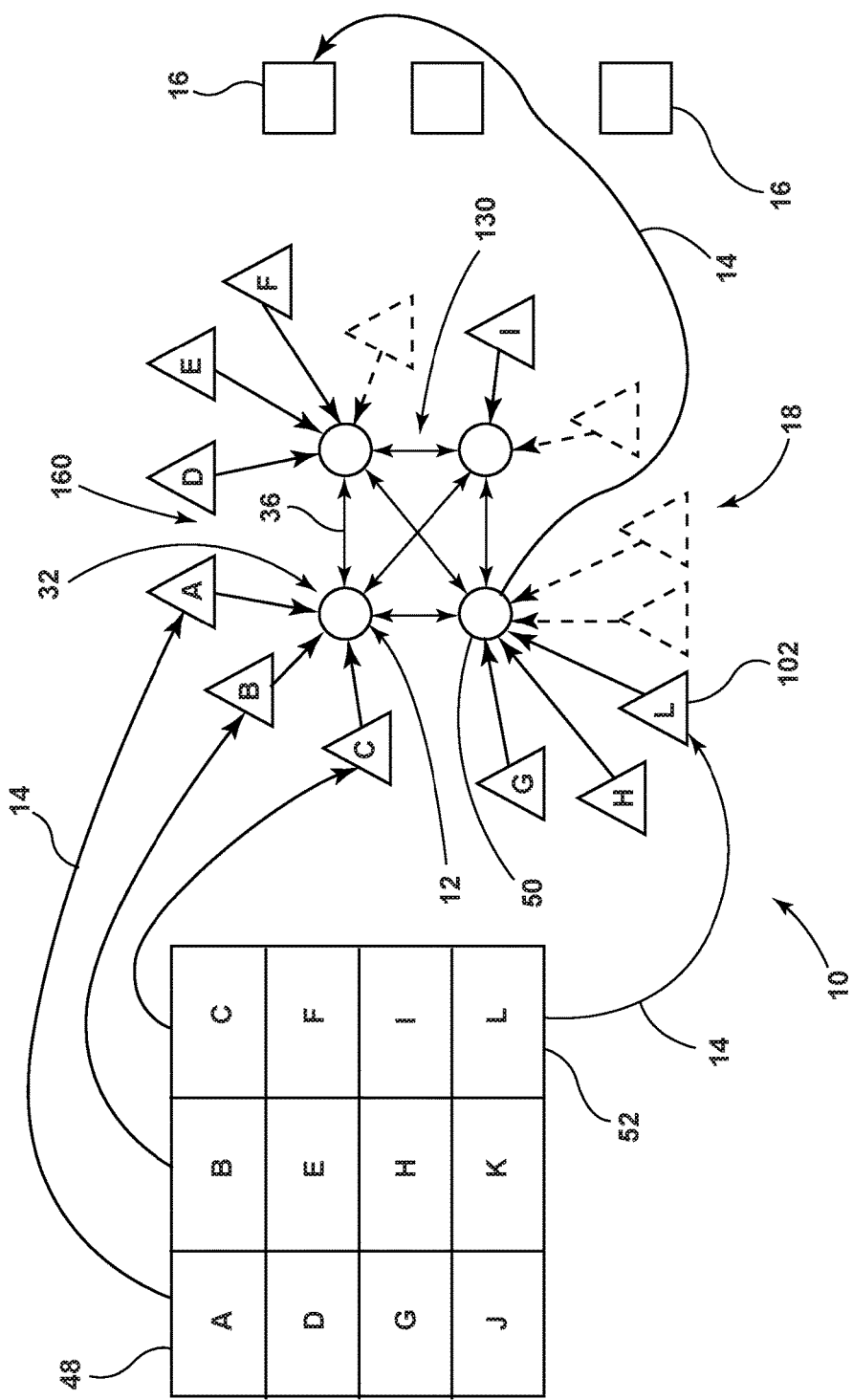
FIG. 5 is a schematic illustration exemplifying the peer-to-peer server network of FIG. 4 illustrating the selection of a potential hosting server among the plurality of servers of the peer-to-peer server network.
Figure 6:
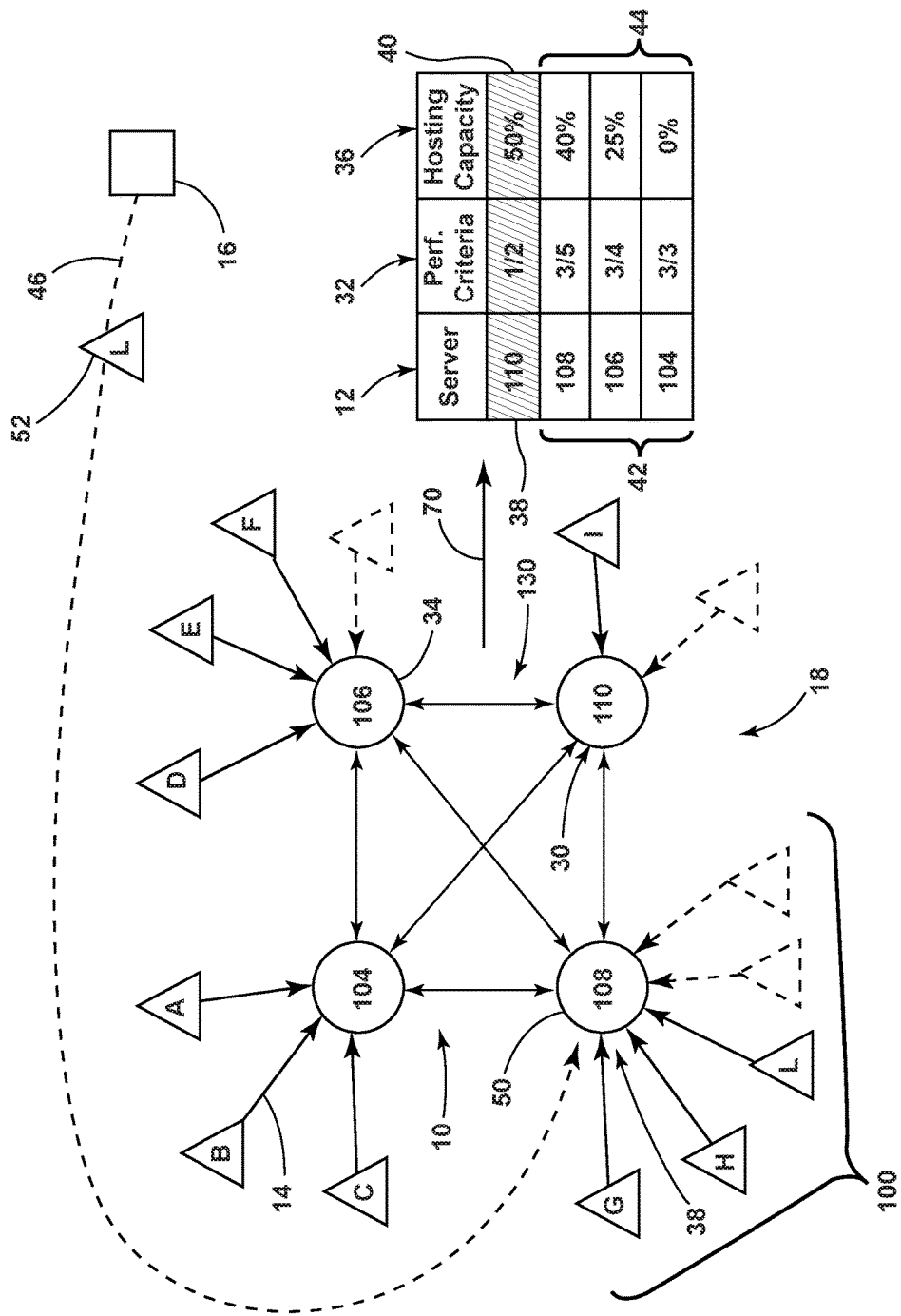
FIG. 6 is a schematic illustration exemplifying the peer-to-peer server network of FIG. 5 and illustrating a re-assessment of the potential hosting server of the peer-to-peer server network after the requested live video feed has been assigned to the active hosting server.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As shown in FIGS. 1-6, reference numeral 10 generally refers to a peer-to-peer server network that contains a plurality of servers 12 that are adapted to place one or more live video feeds 14 in communication with one or more customer terminals 16. The use of the peer-to-peer server network 10 can be adapted to place the live video feed 14 in communication with the customer terminal 16 without recording portions of the live video feed 14 within the peer-to-peer server network 10. According to the various embodiments, a live video feed balancing system 18 for delivering the plurality of live video feeds 14 to the customer terminals 16 includes a plurality of servers 12 that are placed in communication with one another to define a peer-to-peer server network 10. It is contemplated that each server 12 of the peer-to-peer server network 10 is placed in communication with each of the remaining servers 42 of the peer-to-peer server network 10. In this manner, any one server 12 within the peer-to-peer server network 10 is able to communicate with each of the remaining servers 42 of the peer-to-peer server network 10. Accordingly, the peer-to-peer server network 10 contains no "master" server and no "slave" server such as is commonly found in hierarchical server networks.

Referring again to FIGS. 1-6, within the peer-to-peer server network 10, each server 12 defines a monitoring server 30 that monitors at least one corresponding performance criteria 32 of a dedicated server 34 of the peer-to-peer server network 10. Each monitoring server 30 can define a corresponding hosting capacity 36 for the dedicated server 34. It is contemplated that the corresponding hosting capacity 36 of the dedicated server 34 is based on the at least one corresponding performance criteria 32 evaluated by the monitoring server 30. Each monitoring server 30 of the peer-to-peer server network 10 communicates through an outgoing communication the corresponding hosting capacity 36 of the respective dedicated server 34 to the remaining servers 42. In this manner, the corresponding hosting capacities of each server 12 of the peer-to-peer server network 10 are communicated to the remaining servers 42 of the peer-to-peer server network 10 at predetermined intervals. Therefore, each server 12 of the peer-to-peer server network 10 defines both a monitoring server 30 and a dedicated server 34. Accordingly, the monitoring servers 30 of the peer-to-peer server network 10 are adapted to monitor only one dedicated server 34 to evaluate the at least one corresponding performance criteria 32 to arrive at a corresponding hosting capacity 36 for one respective dedicated server 34.

Once the monitoring servers 30 have evaluated the corresponding hosting capacity 36 of the respective dedicated server 34, the plurality of servers 12 of the peer-to-peer server network 10 cooperatively assess the communicated corresponding hosting capacities from all of the monitoring servers 30 to determine a potential hosting server 38. The potential hosting server 38 is defined as having a first hosting capacity 40 and the remaining servers 42 are defined as having a range of second hosting capacities 44. The first hosting capacity 40 is greater than any of the corresponding hosting capacities defined within the range of second hosting capacities 44. Stated another way, the plurality of servers 12 of the peer-to-peer server network 10 cooperatively assess the communicated corresponding hosting capacities to determine which respective dedicated server 34 has a greater corresponding hosting capacity 36 than that of the remaining servers 42 of the peer-to-peer server network 10. The potential hosting server 38, in response to a hosting request 46 for a live video feed 14 from a customer terminal 16, is placed in communication with an image capturing device 48 that delivers the requested live video feed 14. The potential hosting server 38, in response to the request, places the image capturing device 48 in selective communication with the potential hosting server 38 in order to deliver the live video feed 14 to the customer terminal 16. Through this communication between the requested image capturing device 52 and the requested customer terminal 16, the potential hosting server 38 now defines an active hosting server 50 of the peer-to-peer server network 10 with respect to the requested image capturing device 52.

According to the various embodiments, the live video feed 14 can include various types of video and audio information that is captured by the image capturing device 48. Such video and audio information can include, but is not limited to, thermal imaging, closed captioning, and other video and audio information. The live video feed may also include certain status or identification information regarding the particular patient 84 being monitored. Such information may include health-related information (heart rate, blood pressure, condition specific information, and the like), age, the primary language of the patient 84, and other similar information that can be included within or embedded within the live video feed 14

Referring again to FIGS. 1-6, it is contemplated that the monitoring servers 30 of the peer-to-peer server network 10 are adapted to be self-monitoring servers 60, such that the monitoring server 30 and the respective dedicated server 34 being monitored are one and the same. In this manner, each server 12 of the peer-to-peer server network 10 is a self-monitoring server 60 that monitors its own corresponding performance criteria 32 and evaluates this corresponding performance criteria 32 to arrive at a corresponding hosting capacity 36 for the self-monitoring server 60. This information is then communicated from each self-monitoring server 60 to each of the remaining servers 42 of the peer-to-peer server network 10. It is contemplated that the at least one corresponding performance criteria 32 can include, but is not limited to, utilization of the central processing unit, the utilization of the random access memory, the utilization of the network bandwidth, percentage of network utilization, percentage of memory utilization, remaining data capacity, and other similar criteria. It is also contemplated that each of these criteria can be evaluated in the positive (i.e., how much capacity is available) or in the negative (i.e., how much capacity is used). The usage of these corresponding performance criteria 32 allows each of the self-monitoring servers 60 of the peer-to-peer server network 10 to balance the hosting of live video feeds 14 among each of the self-monitoring servers 60 as various hosting requests 46 are made by the various customer terminals 16 with respect to various image capturing devices 48 that deliver the various corresponding live video feeds 14. As will be discussed more fully below, as each hosting request 46 from a customer terminal 16 is made to the peer-to-peer server network 10, the peer-to-peer server network 10 can perform a self-assessment and determine which server 12 of the peer-to-peer server network 10 is best equipped to handle the new live video feed 14 from one or more image capturing devices 48. Similarly, the peer-to-peer server network 10 can periodically perform a self-assessment to determine whether the various servers 12 of the peer-to-peer server network 10 are being utilized in an economical fashion and, if necessary, perform a balancing operation 70 with respect to the various live video feeds 14 being hosted by the servers 12 of the peer-to-peer server network 10.

Referring again to FIGS. 2-6 and 11, it is contemplated that the image capturing device 48 is one of a plurality of image capturing devices 48 that are each in selective communication with the peer-to-peer server network 10. It is contemplated that each image capturing device 48 of the plurality of image capturing devices 48 is able to be hosted or placed in communication with any one server 12 within the peer-to-peer server network 10. Accordingly, hosting functions for a particular image capturing device 48 can be transferred from one server 12 to one of the remaining servers 42 where it is determined to be necessary to perform such a transfer based upon the various assessments and balancing operations 70 performed by the peer-to-peer server network 10. The customer terminal 16 can be one of a plurality of customer terminals 16 that are each in selective communication with the peer-to-peer server network 10. In the case of the customer terminals 16, each customer terminal 16 is in selective communication with any one or more servers 12 of the peer-to-peer server network 10. It is contemplated that any one customer terminal 16 can be in communication with any combination of servers 12 or all of the servers 12 within the peer-to-peer server network 10, depending on the number of live video feeds 14 that are being live-streamed to the particular customer terminal 16 via the servers 12 of the peer-to-peer server network 10.

The customer terminals 16 may be characterized as processor-driven monitors 80 that display the various live video feeds 14 of corresponding image capturing devices 48. In certain situations, a person 82 can be tasked with observing the monitor 80 having the displayed live video feeds 14. This person 82, typically, looks to see if the patient 84 is in their bed 86 in their hospital room 88. If the patient 84 attempts to get out of bed 86, when not authorized to do so, the person 82 viewing the live video feed 14 for that patient 84 can alert a medical staff 90 near the patient 84 to provide assistance. The image capturing devices 48 can include standard video cameras as well as motion sensors, microphones, speakers, night vision capabilities and other communications equipment to monitor the patient 84 and provide a live video feed 14 to the customer terminal 16 via the peer-to-peer server network 10.

Referring now to FIGS. 2-6 and 11, the peer-to-peer server network 10 is adapted to provide hosting capabilities for one or more live video feeds 14 from respective image capturing devices 48. It is contemplated that the corresponding total hosting capacity 100 of each server 12 can correspond to a certain number of hosted feeds 102 that a particular server 12 is able to handle at any particular time. By way of example, and not limitation, a first server within the peer-to-peer server network 10 may be able to provide for a total hosting capacity 100 of up to three hosted feeds 102. A second server 106 within the peer-to-peer server network 10 may be able to provide for four hosted feeds 102, a third server 108 within the peer-to-peer server network 10 may be able to provide for five hosted feeds 102 and a fourth server 110 within the peer-to-peer server network 10 may provide for two hosted feeds 102. It should be understood that the total hosting capacity 100 of each server 12 listed herein is exemplary in nature and a server 12 of the peer-to-peer server network 10, in actuality, may be able to host large numbers of hosted feeds 102. The exact number of hosted feeds 102 can vary depending upon the configuration of the particular server 12 within the peer-to-peer server network 10.

As discussed above, during operation of the peer-to-peer server network 10, each server 12 within the peer-to-peer server network 10 continually, or periodically, communicates at least one of the corresponding performance criteria 32 and/or the corresponding hosting capacity 36 for the self-monitoring server 60 to the remaining servers 42 of the peer-to-peer server network 10. Accordingly, at any one time, the servers 12 of the peer-to-peer server network 10 cooperatively determine a potential hosting server 38, such that when a hosting request 46 is received from a customer terminal 16, the potential hosting server 38 is ready to act as the active hosting server 50 for the particular live video feed 14. Throughout performance of the peer-to-peer server network 10, various customer terminals 16 can make hosting requests 46 for a particular live video feed 14 from a corresponding image capturing device 48. Termination requests 120 may also be received for stopping a live video feed 14 for a particular image capturing device 48. As these hosting requests 46 and termination requests 120 are received, the peer-to-peer server network 10 performs another assessment or balancing operation 70 to reevaluate the hosting capabilities of each self-monitoring server 60 to determine the potential hosting server 38 at any particular time. As each hosting request 46 and termination request 120 is received, the identity of the potential hosting server 38 can change from one server 12 to another server 12 based upon the evaluation of the corresponding performance criteria 32 of the servers 12 of the peer-to-peer server network 10.

Referring again to FIGS. 2-6 and 11, by way of example, and not limitation, the peer-to-peer server network 10 exemplified in FIGS. 2 and 3 show first, second, third and fourth servers 104, 106, 108, 110 of a self-monitoring type that make up the peer-to-peer server network 10. The exemplified peer-to-peer server network 10 shows that image capturing devices 48 (labeled A-J) are currently hosted by one of the first through fourth servers 104, 106, 108, 110, which can be of the self-monitoring variety. Each of these servers 12, in turn, is in communication with at least one customer terminal 16 of the plurality of customer terminals 16. When a hosting request 46 from one of the customer terminals 16 for the live video feed 14 corresponding to image capturing device 48 (L) is sent to the peer-to-peer server network 10, the peer-to-peer server network 10 conducts a self-assessment or balancing operation 70 to determine the potential hosting server 38. It is contemplated that the self-assessed balancing operation 70 may have occurred before the hosting request 46 arrived such that the peer-to-peer server network 10 has already determined the potential hosting server 38. When the hosting request 46 for image capturing device 48 (L) is sent to the peer-to-peer server network 10, the peer-to-peer server network 10 determines that the third server 108 of the peer-to-peer server network 10 is the potential hosting server 38 at that time. This determination may be made based upon the fact that the third hosting server 108, as exemplified in image, has the greatest corresponding hosting capacity 36 of the first through fourth self-monitoring servers 104, 106, 108, 110. This can be expressed as the corresponding hosting capacity 36 in relation to the total hosting capacity 100 for each server 12. The third server 108 is then placed in communication with both the image capturing device 48 (L) as well as the customer terminal 16 that sent the hosting request 46 with respect to image capturing device 48 (L). In this manner, the third server 108 of the peer-to-peer server network 10 has become the active hosting server 50 with respect to image capturing device 48 (L). After image capturing device 48 (L) has been assigned to an active hosting server 50, the peer-to-peer server network 10 may perform another self-assessed balancing operation 70 to redefine which server 12 of the peer-to-peer server network 10 is the potential hosting server 38 in the event of another hosting request 46.

Referring again to FIGS. 2-6, 10 and 11, where the peer-to-peer server network 10 receives one or more termination requests 120, a particular server 12 may be left with a corresponding hosting capacity 36 that is far greater or less than the remaining servers 12 of the peer-to-peer server network 10. In such a condition, a periodic self-assessed balancing operation 70 of the peer-to-peer server network 10 may result in a rebalancing of the hosted feeds 102 of the servers 12 of the peer-to-peer server network 10. One of the servers 12 that is particularly loaded with hosted feeds 102 may have one of those hosted feeds 102 transferred to a server 12 having a much higher corresponding hosting capacity 36. This balancing function can help to ensure that the various servers 12 of the peer-to-peer server network 10 are not overtaxed relative to the remaining servers 12 of the peer-to-peer server network 10.

It is contemplated that the transition of hosted feeds 102 from one server 12 to one of the remaining servers 12 can be performed by the peer-to-peer server network 10 itself. In this manner, the various servers 12 of the peer-to-peer server network 10 can act as a cooperative processor 130 that initiates each balancing operation 70, receives each hosting request 46 and termination request 120, and performs various computing operations during performance of the peer-to-peer server network 10.

According to the various embodiments, it is contemplated that the various self-monitoring servers 60 of the peer-to-peer server network 10 are not necessarily located in a single physical location. It is contemplated that the various servers 12 can be positioned in two or more different and/or separate geographic locations, where the various servers 12 are placed in communication via various network connections, cloud computing connections, and other similar data connections. Additionally, it is contemplated that each server 12 of the peer-to-peer server network 10 can be limited to only hosting the various live video feeds 14 from the respective image capturing devices 48. In such an embodiment, no recording or buffering of the live video feeds 14 is conducting by the servers 12, and each server 12 acts as a conduit or gated passage through which the image capturing device 48 can be placed in communication with one or more customer terminals 16. It is also contemplated that recording and/or "buffering" functions may be performed at the customer terminal 16. It is also contemplated that buffering and/or recording may be conducted by one or more servers 12 of a peer-to-peer server network 10. Such buffering and recording functions can be stored directly on the self-monitoring server 60 acting as the active hosting server 50 in communication with the corresponding image capturing device 48. It is also contemplated that a separate data recording device in communication with the peer-to-peer server network 10 can be utilized for buffering and/or recording functions. The buffered and/or recorded data can be available to any one or more of the customer terminals 16. In various embodiments, wherein the active hosting server 50 performs the buffering and/or recording functions, the buffered and/or recorded data can be transferred to a different self-monitoring server 60 in response to a change in hosting designations as a result of a balancing operation 70.

Referring now to FIGS. 2-11, it is contemplated that one or more self-monitoring servers 60 of the peer-to-peer server network 10 may experience a failure mode 140. A failure mode 140 of the peer-to-peer server network 10 can be defined by the absence of a communication from any one or more of the servers 12 to the remaining servers 12 in response to the performance of the balancing operation 70. Where no communication is received by the remaining servers 12, a complete performance of the balancing operation 70 of all of the servers 12 of the peer-to-peer server network 10 is not possible. In such a failure mode 140, it is contemplated that the remaining servers 12 of the peer-to-peer server network 10 may initiate a failure mode 140 response to reallocate the hosted feeds 102 that are currently being hosted by the server 12 that is experiencing the failure mode 140 or the off-line server 142. In the failure mode 140, the remaining servers 12 perform a balancing operation 70 without including the off-line server 142. The remaining servers 12 determine a potential hosting server 38 with respect to the remaining servers 12 by evaluating the corresponding hosting capacity 36 of the remaining servers 12. A hosted feed 102 from the off-line server 142 is then automatically transferred to the potential hosting server 38 to define an active hosting server 50 with respect to the reallocated hosted feed 102. This process is repeated for each hosted feed 102 being hosted by the off-line server 142 and is repeated until all of the feeds hosted by the off-line server 142 have been reallocated to active hosting servers 50 among the remaining servers 12 of the peer-to-peer server network 10. At the outset of the failure mode 140, a failure signal 150 may be sent to a service module 152 or service provider such that maintenance can be performed on the off-line server 142 and the peer-to-peer server network 10. When the off-line server 142 is brought back on-line, that server 12 is then re-inserted into the peer-to-peer server network 10 and the balancing operation 70 is again performed to re-balance the system after the once off-line server 142 is reinserted into the peer-to-peer server network 10. This failure mode 140 is initiated in order to minimize the amount of downtime of hosted live video feeds 14 experienced by the customer terminals 16 in the event of a failure within the peer-to-peer server network 10.

In conventional systems, a failure at one of the servers 12 of a hierarchical server network can necessitate the manual transfer of video feeds 14 from a failed server 12 to an on-line server. This operation can take a substantial amount of time. This time can be critical where a particular patient 84 requires around-the-clock monitoring.

Figure 7:
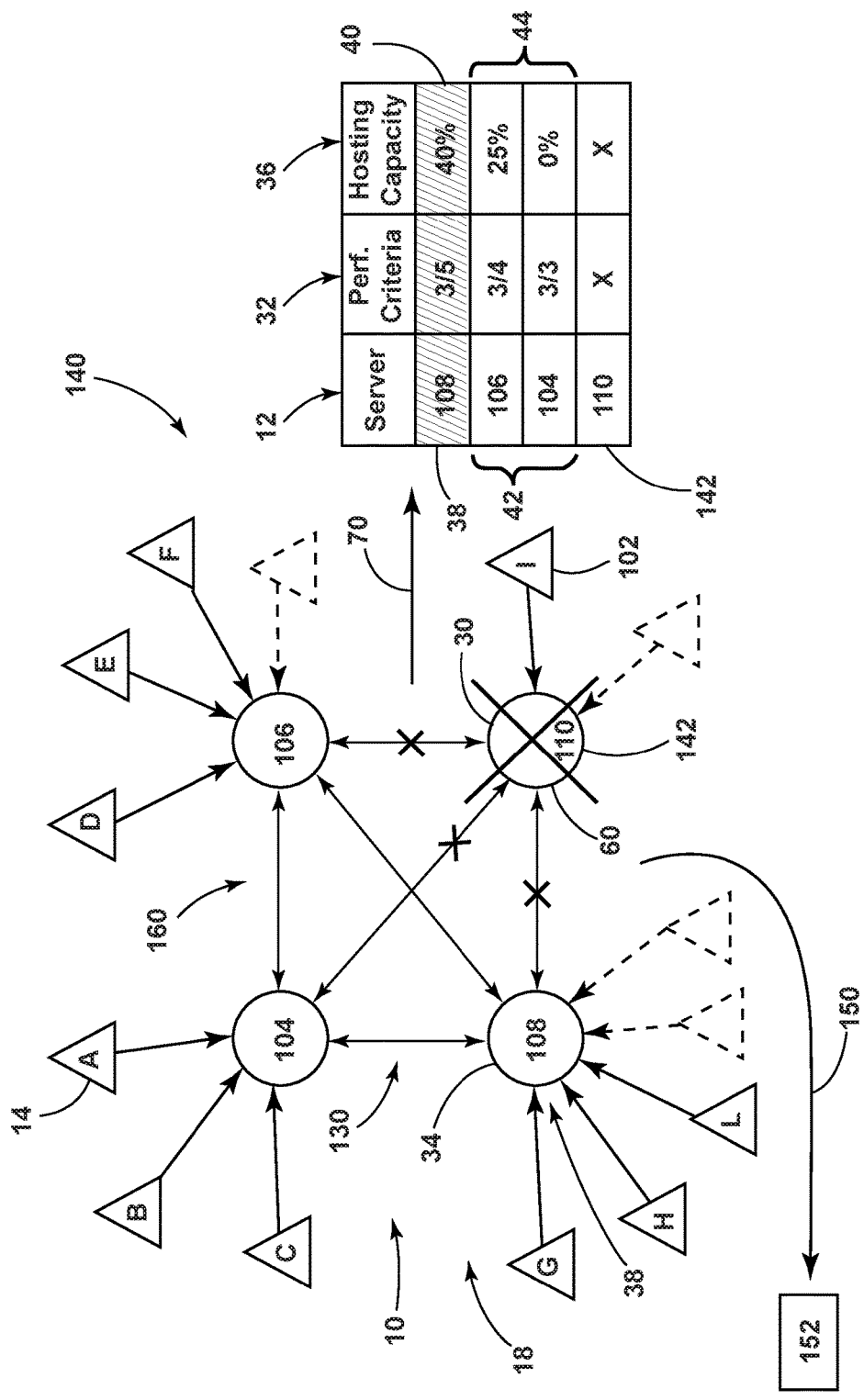
FIG. 7 is a schematic illustration of the peer-to-peer server network of FIG. 2 exemplifying a failure mode of at least one server of the peer-to-peer server network.
Figure 8:
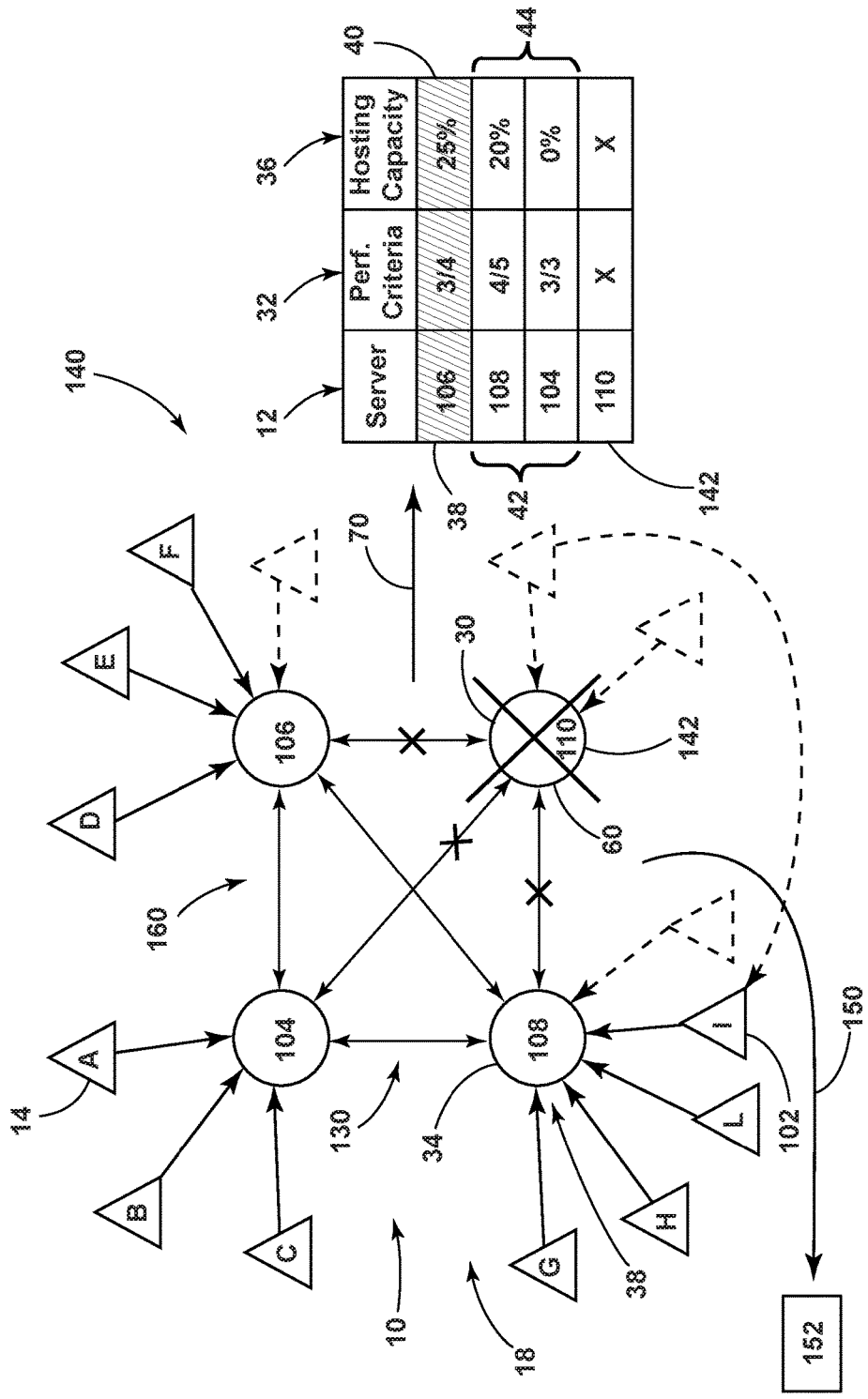
FIG. 8 is a schematic illustration of the peer-to-peer server network of FIG. 7 exemplifying a re-assessment of the servers of the peer-to-peer server network that do not define the failure mode.
Figure 9:
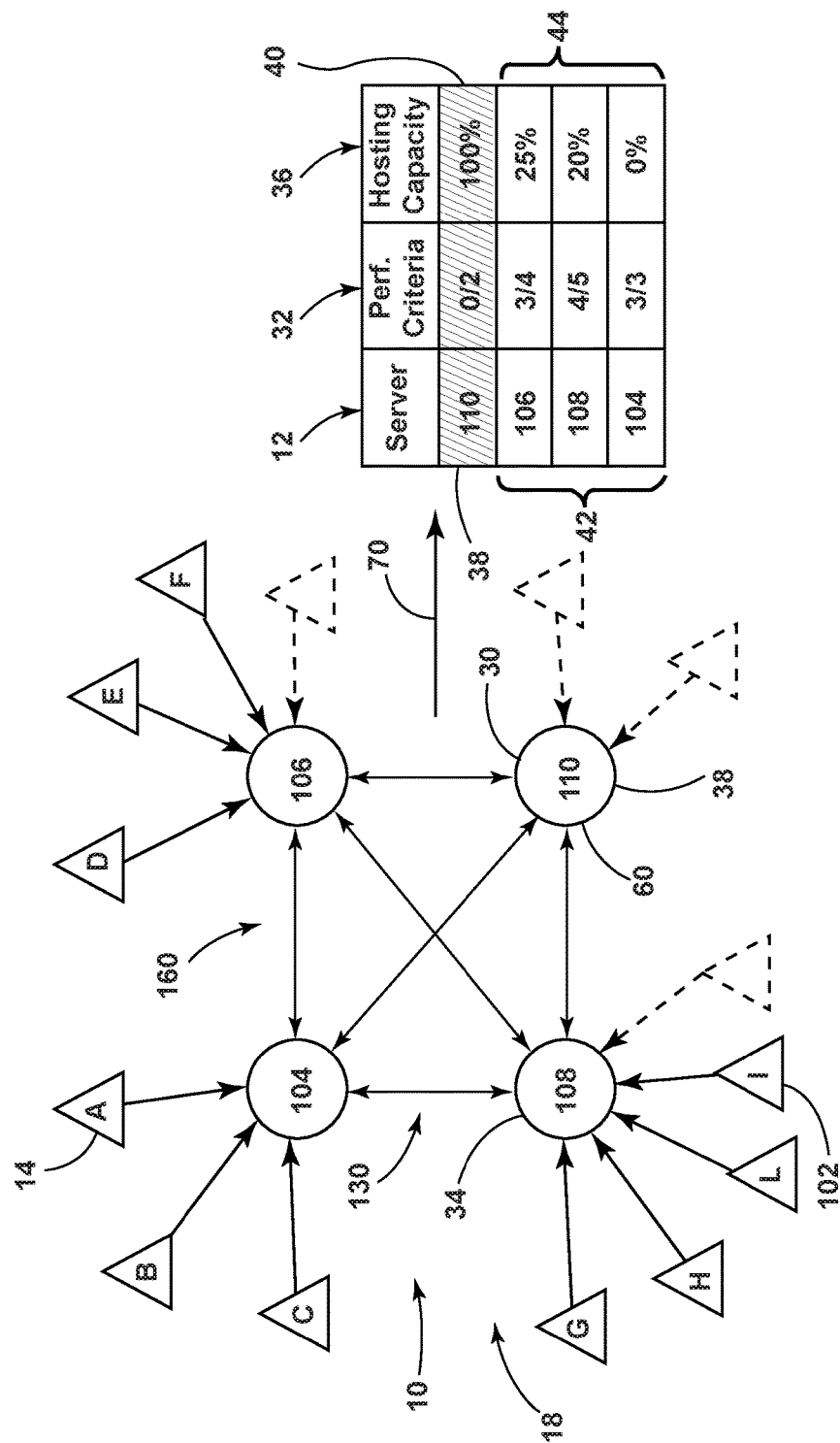
FIG. 9 is a schematic illustration of the peer-to-peer server network of FIG. 8 exemplifying a re-allocation of live video feeds after the off-line server is reinserted into the peer-to-peer server network.
Figure 10:
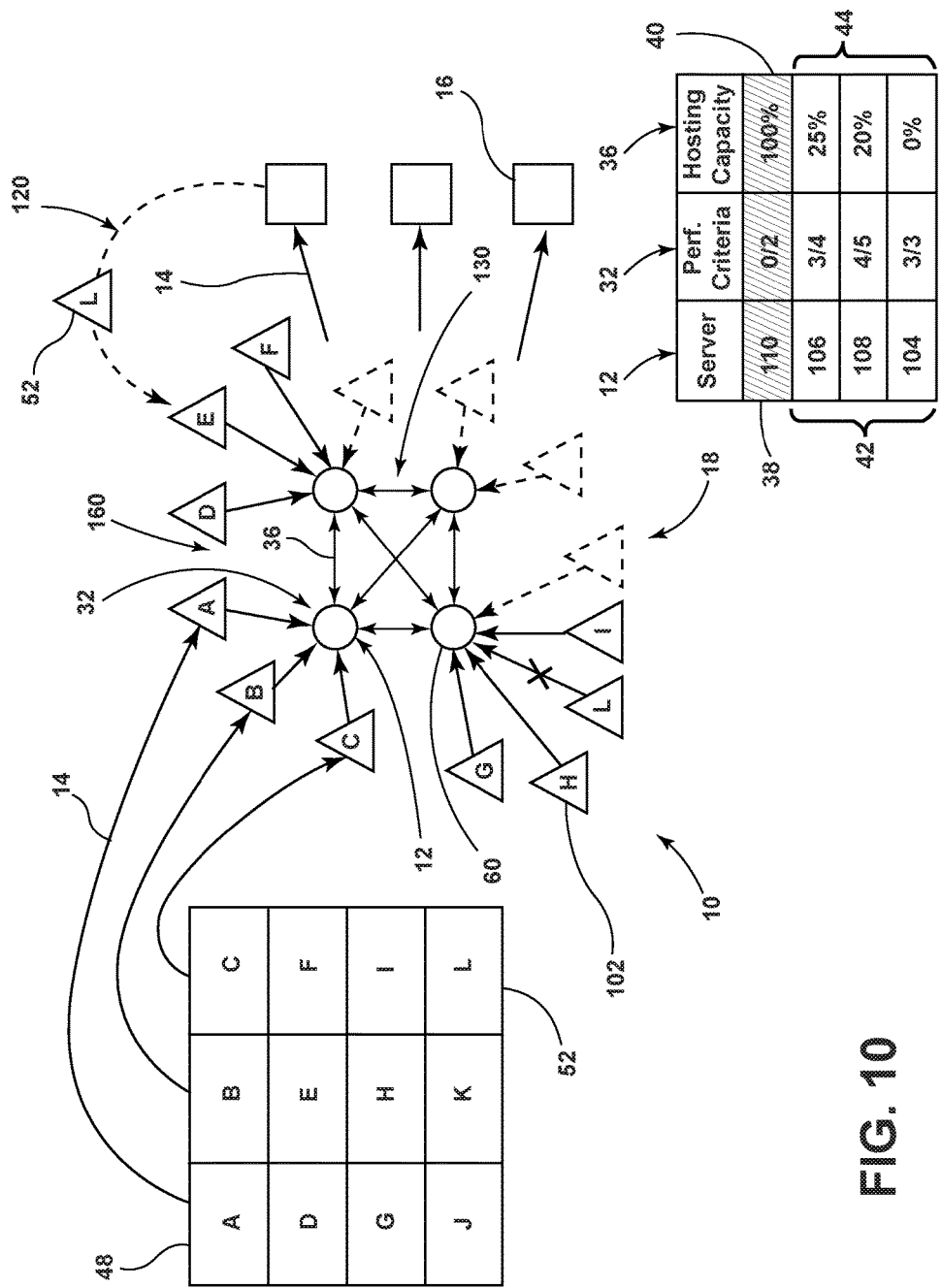
FIG. 10 is a schematic illustration of the peer-to-peer server network of FIG. 9 exemplifying a termination request sent to the peer-to-peer server network to stop a live video feed.
Figure 11:
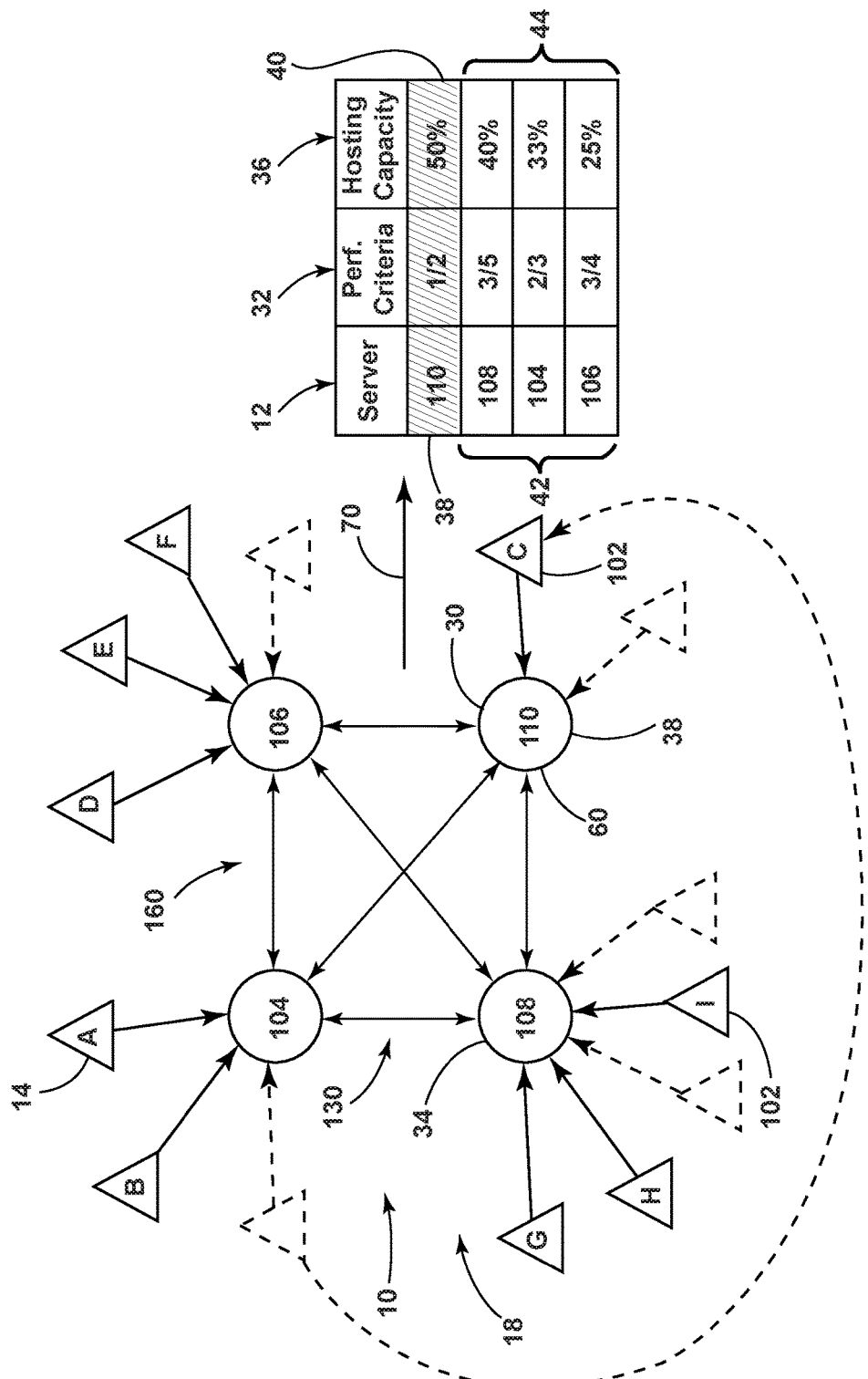
FIG. 11 is a schematic illustration of the peer-to-peer server network of FIG. 10 exemplifying performance of a balancing operation of the peer-to-peer server network.
Figure 12:
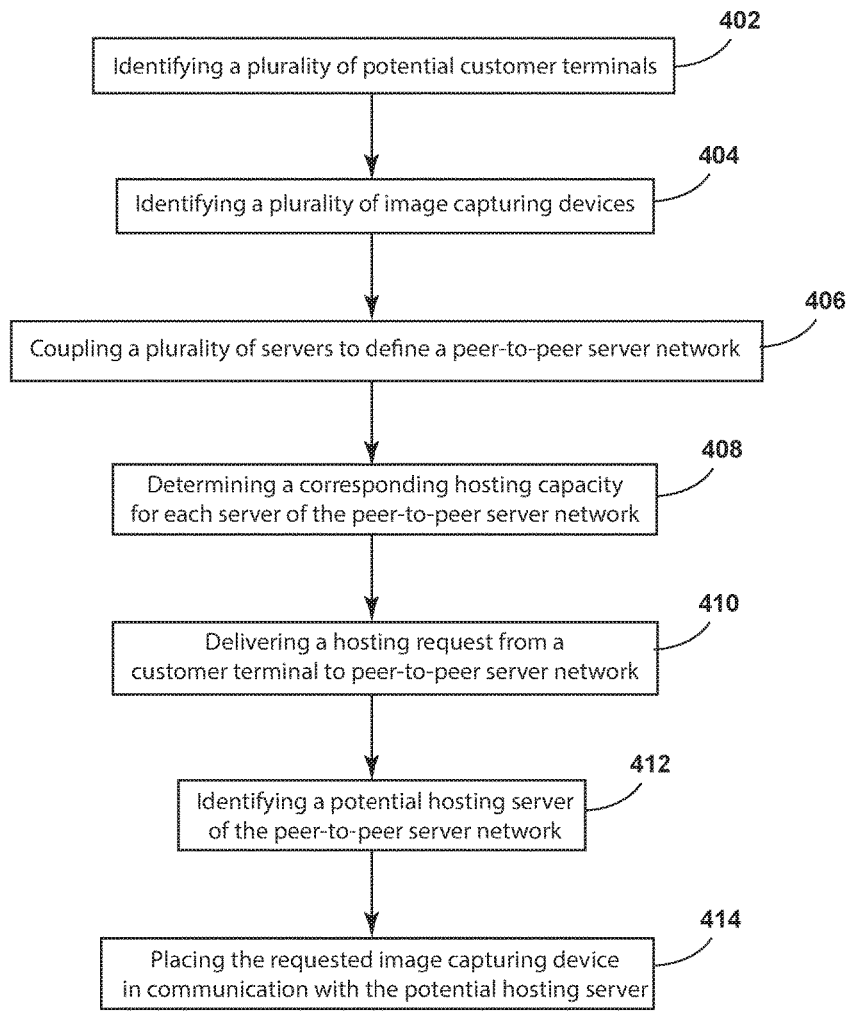
FIG. 12 is a flow diagram exemplifying a method for live streaming a plurality of server-hosted video feeds using a peer-to-peer server network.
Figure 13:
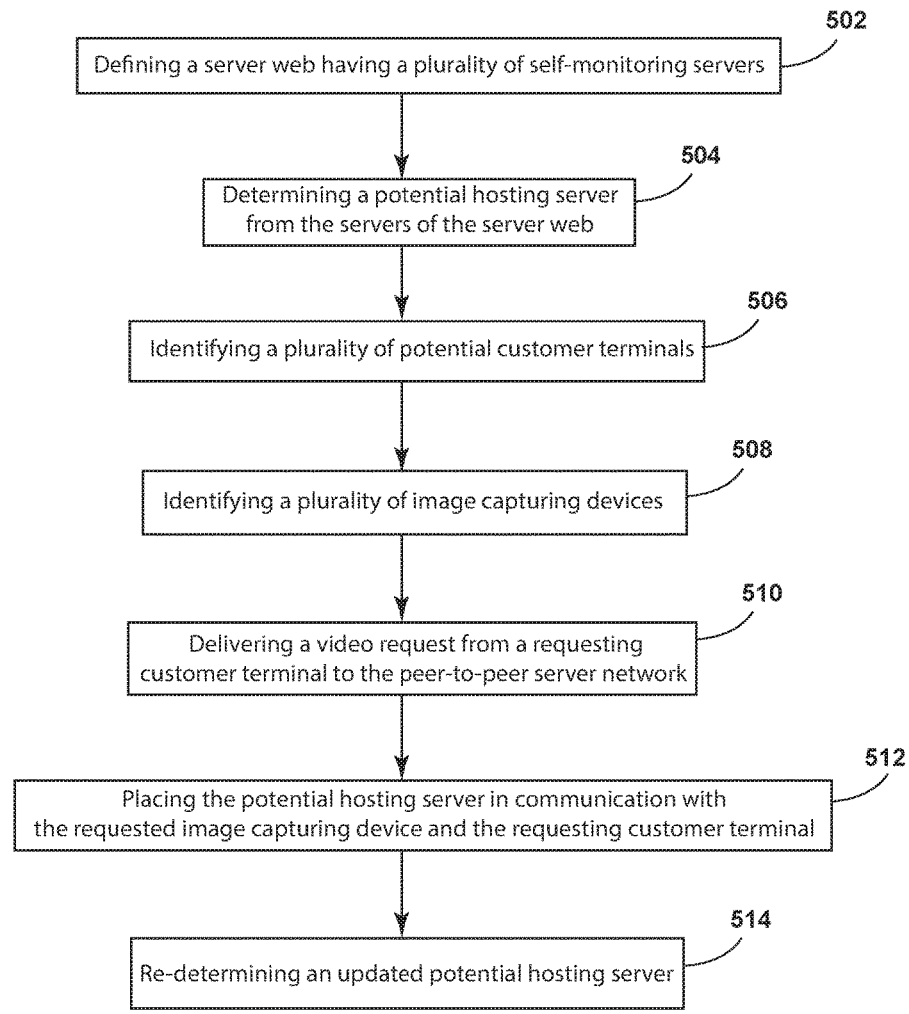
FIG. 13 is a flow diagram exemplifying a method for live streaming a plurality of server-hosted video feeds using a peer-to-peer server network.
Figure 14:
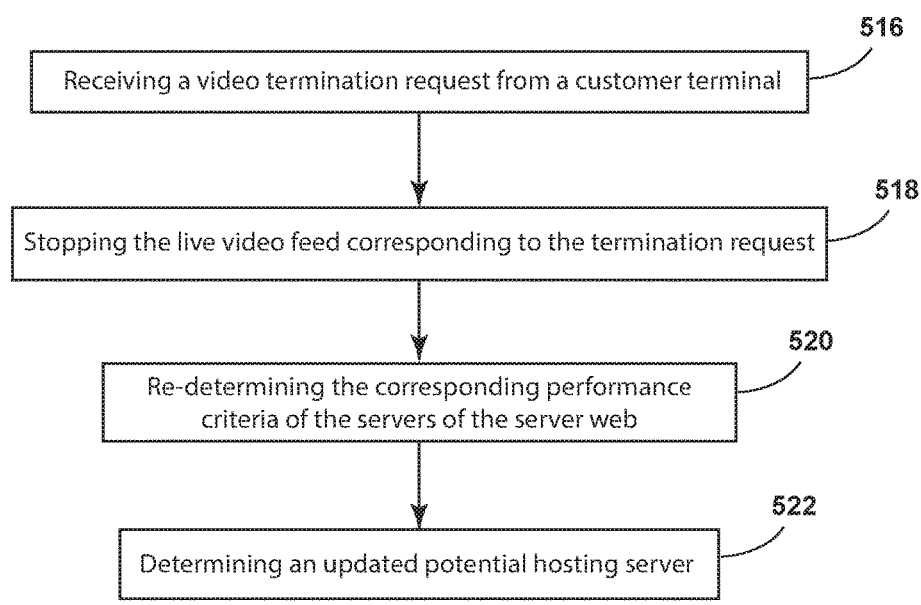
FIG. 14 is a flow diagram further exemplifying the method exemplified in FIG. 13 for live streaming a plurality of server-hosted video feeds using a peer-to-peer server network.
Figure 15:
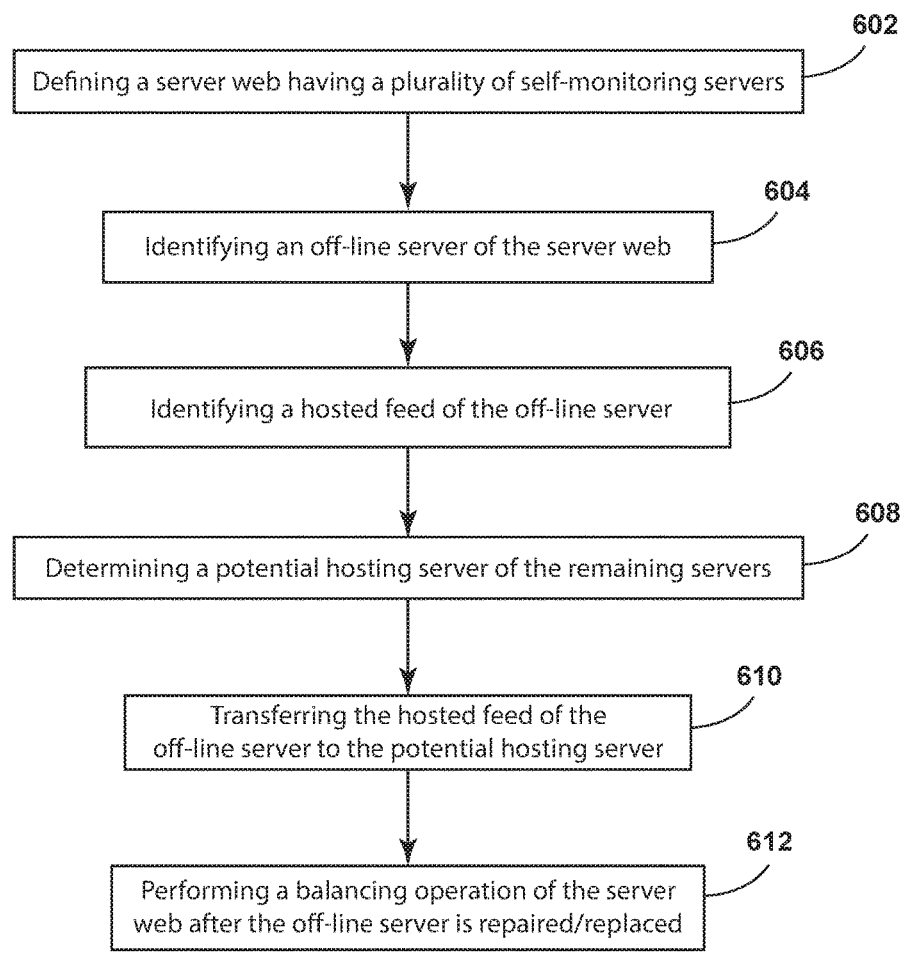
FIG. 15 is a schematic flow diagram illustrating a method for live streaming a plurality of server-hosted video feeds during a failure mode of one of the servers of a peer-to-peer server network.

In the event of failure mode 140, as exemplified in FIGS. 7-9, it is contemplated that certain live video feeds 14 from various image capturing devices 48 can be assigned a priority level. A high priority can be placed upon an image capturing device 48 that is used to monitor a patient 84 that may require high levels of monitoring. Lower priority image capturing devices 48 may be assigned for health care patients 84 requiring less monitoring or are of a lower risk when not being monitored. In the event of a failure mode 140, the higher priority image capturing devices 48 may be transferred from the off-line server 142 to the new potential hosting server 38 among the remaining servers 12, before the lower priority image capturing devices 48. In this manner, the amount of downtime for each of the image capturing devices 48 can be kept to a minimum for high-priority image capturing devices 48. While not significantly longer in time, a lesser priority image capturing device 48 may be transferred after higher priority image capturing devices 48. It is contemplated that the priority level assigned to each image capturing device 48 may be assessed by the health care professional monitoring the particular patient 84. A history of incidents for a particular patient 84 can also factor into the assessment of a particular priority level for a respective video monitoring device. As an example, a patient 84 that frequently tries to get out of bed 86 when instructed to remain in bed 86 may require a higher priority level than a patient 84 that has fewer or no incidents of attempting to get out of bed 86 when instructed not to do so.

Referring now to FIGS. 1-12, having described various embodiments and aspects of a balancing system 18 for hosting live video feeds 14, a method 400 is disclosed for live streaming a plurality of server-hosted live video feeds 14 using a peer-to-peer server network 10. According to the method 400, a plurality of potential customer terminals 16 are identified by a peer-to-peer server network 10 (step 402). The potential customer terminals 16 can be represented by a paid service or fee-based service that is required in order to utilize the peer-to-peer server network 10. Once the potential customer terminals 16 are identified, each of these potential customer terminals 16 are placed in selective communication with one or more servers 12 of the peer-to-peer server network 10. The identification of a particular customer terminal 16 can occur at various times in the operation of the peer-to-peer server network 10. It is contemplated that the identification step 402 can occur in response to a hosting request 46, activating a subscription service involving the peer-to-peer server network 10, connection with at least one server 12 of the peer-to-peer server network 10, combinations thereof, and other similar events that may occur during operation of the peer-to-peer server network 10. A plurality of image capturing devices 48 are also identified by the peer-to-peer server network 10 (step 404). The various image capturing devices 48 can be owned or operated by various health care providers such as hospitals, medical facilities, nursing homes, hospice providers, and other similar health care providers. As discussed above, the plurality of servers 12 are coupled to define the peer-to-peer server network 10 (step 406). Again, each server 12 of the peer-to-peer server network 10 is in communication with each remaining server 12 of the peer-to-peer server network 10. A corresponding hosting capacity 36 is determined for each server 12 of the plurality of servers 12 within the peer-to-peer server network 10 (step 408). Each server 12 within the peer-to-peer server network 10 defines a monitoring server 30 that operates to monitor at least one performance criteria 32 of one corresponding monitored or dedicated server 34 within the peer-to-peer server network 10. Accordingly, each monitoring server 30 assigns a corresponding hosting capacity 36 for the corresponding dedicated server 34 based upon the at least one performance criteria 32. The corresponding hosting capacity 36 for each corresponding dedicated server 34 of the peer-to-peer server network 10 is then communicated to each remaining server 12 of the peer-to-peer server network 10. As discussed above, this step 408 of determining a hosting capacity 36 can then be performed continuously, periodically, in response to a hosting request 46 or termination request 120, in response to a failure mode 140 indication, combinations thereof, or other periodic times as dictated by the peer-to-peer server network 10.

Referring again to FIGS. 1-10, according to the method 400, a video hosting request 46 is delivered from a requesting customer terminal 16 of the plurality of potential customer terminals 16 to the peer-to-peer server network 10 (step 410). The hosting request 46 identifies a requested image capturing device 52 of the plurality of image capturing devices 48 that is to be placed in communication with the requesting customer terminal 16 via a potential hosting server 38 of the peer-to-peer server network 10. The potential hosting server 38 is then identified with respect to the hosting request 46 (step 412). It is contemplated that the hosting server or potential hosting server 38 is defined as the server 12 having a corresponding first hosting capacity 40 as opposed to the remaining servers 12 which are defined as having a range of corresponding second hosting capacities 44. As discussed above, the corresponding first hosting capacity 40 is greater than any of the corresponding hosting capacities within the range of corresponding second hosting capacities 44. The requested image capturing device 52 is then placed in communication with the potential hosting server 38 and the potential hosting server 38 is placed in communication with the requesting customer terminal 16 to deliver a live video feed 14 from the requested image capturing device 52 to the requested customer terminal 16 (step 414). Accordingly, the potential hosting server 38 is then defined as the active hosting server 50 with respect to the particular image capturing device 48.

Referring now to FIGS. 2-11, 13 and 14, a method 500 for live streaming a plurality of server-hosted live video feeds 14 using a peer-to-peer server network 10 is also disclosed. According to the method 500, a server web 160 in the form of a peer-to-peer server network 10 is defined by a plurality of servers 12, typically, self-monitoring servers 60, of the peer-to-peer server network 10 (step 502). As discussed above, each server 12 of the server web 160 is in communication with each remaining server 12 of the server web 160 and each server 12 monitors at least one corresponding performance criteria 32 of the respective dedicated server 34. It is also contemplated that each server 12 communicates the corresponding performance criteria 32 to each remaining server 12 of the server web 160. It is contemplated that the server web 160 can correspond to the peer-to-peer server network 10 disclosed herein. A potential hosting server 38 is determined by the server web 160 (step 504). The servers 12 of the server web 160 assess each corresponding performance criteria 32 to define a first performance criteria 32 that corresponds to the potential hosting server 38. Each remaining performance criteria 32 of the remaining servers 12 collectively defines a range of second performance criteria 32. As discussed above, this self-assessment, or balancing operation 70, by the server web 160 identifies the potential hosting server 38 as the server 12 having the greatest corresponding hosting capacity 36 for handling a subsequent or previously received hosting request 46. According to the method 500, at least one or a plurality of potential customer terminals 16 are identified (step 506). At least one or a plurality of image capturing devices 48 are also identified (step 508). A video hosting request 46 is delivered from a requesting customer terminal 16 of the plurality of customer terminals 16 to the peer-to-peer server network 10 (step 510). It is contemplated that the video hosting request 46 identifies a requested image capturing device 52 or a plurality of requested image capturing devices 52 to be placed in communication with the requested customer terminal 16 via the potential hosting server 38 of the peer-to-peer server network 10. The potential hosting server 38 is then placed in communication with the requested image capturing device 52 and the requested customer terminal 16 (step 512). In this manner, the potential hosting server 38 then defines an active hosting server 50 that defines communication between the requested image capturing device 52 and the requested customer terminal 16. An updated potential hosting server 38 is then redetermined by the peer-to-peer server network 10 (step 514). In this manner, the active hosting server 50 and the remaining self-monitoring servers 60 of the server web 160 communicate update corresponding performance criteria 32 to each other self-monitoring server 60 of the server web 160 to redefine an updated corresponding first criteria and an updated range of corresponding second performance criteria 32. Accordingly, the identity of the potential hosting server 38 may change to a different server 12 within the server web 160.

Referring again to FIGS. 2-9, 11 and 12, according to the method 500, a video termination request 120 can be received from the requesting customer terminal 16 that is in communication with the requested image capturing device 52 via the active hosting server 50 (step 516). It is contemplated that the termination request 120 relates to selectively terminating communication between the requesting customer terminal 16 and the requested image capturing device 52. In response to the termination request 120, the live video feed 14 is stopped, interrupted, or otherwise terminated (step 518). The corresponding performance criteria 32 for each self-monitoring server 60 in the server web 160 is then redetermined after termination of the live video feed 14 (step 520). The updated potential hosting server 38 is then re-identified (step 522). The previously active hosting server 50 and the remaining self-monitoring servers 60 communicate updated corresponding performance criteria 32 to each other self-monitoring server 60 of the server web 160 to redefine an updated first corresponding performance criteria 32 and an updated second range of corresponding performance criteria 32. Again, the identity of the potential hosting server 38 may change after performance of the termination request 120 from the requesting customer terminal 16.

Referring now to FIGS. 1-11 and 15, a method 600 is disclosed for operating a peer-to-peer server network 10 in the event of a failure mode 140 of the peer-to-peer server network 10. According to the method 600, a server web 160 having a plurality of self-monitoring servers 60 is defined (step 602). During operation of the server web 160, one of the self-monitoring servers 60 may define a failure mode 140. In this failure mode 140, one of the self-monitoring servers 60 may be identified as an off-line server 142 of the server web 160 (step 604). As discussed herein, an off-line server 142 may be defined as a self-monitoring server 60 that fails to transmit a communication regarding at least one of the corresponding performance criteria 32 or the corresponding hosting capacity 36 to the remaining servers 42 of the server web 160. Other indications that a self-monitoring server 60 or other type of server 12 is defining an off-line server 142 can include, but are not limited to, a power failure, physical damage to the off-line server 142, other communications failure involving the off-line server 142, combinations thereof, and other similar events indicative of a self-monitoring server 60 or other type of server 12 of the server web 160 not functioning properly. Once the off-line server 142 is identified, the hosted feeds 102 of the off-line server 142 are then identified (step 606). The potential hosting server 38 among the remaining servers 42, that are free of or do not define the failure mode 140, of the server web 160 is then identified to take over the hosting functions with respect to the hosted feed 102 of the off-line server 142 (step 608). Once the potential hosting server 38 is identified, the hosted feed 102 of the off-line server 142 is transferred to the potential hosting server 38 that now defines the active hosting server 50 as to the transferred hosted feed 102 (step 610). It is contemplated that the balancing operation 70 can then be performed again to re-determine the potential hosting server 38 with respect to the next hosted feed 102 to be transferred from the off-line server 142, if any. While all of the hosted feeds 102 are being transferred away from the off-line server 142, the off-line server 142 can be repaired. Once repaired, the newly repaired self-monitoring server 60 is reinserted into the server web 160 and the balancing operation 70 is again conducted to apportion the various hosted feeds 102 of the server web 160 among the self-monitoring servers 60 of the server web 160 (step 612).

It is contemplated that during the course of performance of a particular peer-to-peer server network 10, additional servers 12 can be added to the peer-to-peer server network 10. Upon the addition of a new server 12, it is contemplated that a self-assessed balancing operation 70 of the peer-to-peer server network 10 is performed to balance the hosted feeds 102 of the peer-to-peer server network 10 among the various servers 12 of the peer-to-peer server network 10. The use of the peer-to-peer server network 10 is adapted to serve a large number of image capturing devices 48 having a number that exceeds or potentially greatly exceeds the number of servers 12 in the peer-to-peer server network 10. Similarly, the number of customer terminals 16 of the plurality of customer terminals 16 can exceed or can also greatly exceed the number of servers 12 in the peer-to-peer server network 10.

According to the various embodiments, the use of the peer-to-peer server network 10 serves to provide a balanced hosting system through which downtime can be minimized as a result of failure, overloading or maintenance of the various servers 12 within the peer-to-peer server network 10. The apparatus and methods described herein are adapted to automatically transfer hosted feeds 102 from one server 12 to another in response to various inputs and events that are experienced by the peer-to-peer server network 10. Minimizing the downtime in the posted feeds delivered by the peer-to-peer server network 10 can maintain a consistent surveillance regimen of health care patients 84, and also health care providers that can decrease the incidents of patients 84 being injured when attempting to get out of bed 86 when not instructed to do so. The use of the peer-to-peer server network 10 can also allow for a single customer terminal 16 to monitor multiple live video feeds 14, thereby decreasing the amount of manpower necessary to monitor healthcare patients 84.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A live-feed video balancing system comprising:
   a plurality of servers placed in communication to define a peer-to-peer server network, wherein each server of the peer-to-peer server network is placed in communication with each remaining server of the peer-to-peer server network, and wherein:
      each server of the peer-to-peer server network defines a monitoring server that monitors at least one corresponding performance criteria of a dedicated server of the peer-to-peer server network;
      each monitoring server defines a corresponding hosting capacity for the dedicated server, wherein the corresponding hosting capacity is based on the at least one corresponding performance criteria;
      each monitoring server communicates the corresponding hosting capacity of the dedicated server to the remaining servers such that the corresponding hosting capacity is communicated to the remaining servers at predetermined intervals; and
      the plurality of servers of the peer-to-peer server network cooperatively assess the communicated corresponding hosting capacities from all of the monitoring servers to determine a potential hosting server, wherein the potential hosting server has a first hosting capacity and the remaining servers have a range of second hosting capacities, wherein the first hosting capacity is greater than any of the corresponding hosting capacities within the range of second hosting capacities;
      the potential hosting server, in response to a request for a live video feed from a customer terminal, is placed in communication with an image capturing device that delivers the live video feed, the potential hosting server being adapted to place the image capturing device in selective communication with the potential hosting server to deliver the live video feed to the customer terminal to define an active hosting server.

2. The live-feed video balancing system of claim 1, wherein the monitoring server also defines the dedicated server such that each monitoring server defines a self-monitoring server of the peer-to-peer server network that communicates the corresponding hosting capacity of the self-monitoring server to the remaining servers of the peer-to-peer server network.

3. The live-feed video balancing system of claim 1, wherein the image capturing device is one of a plurality of image capturing devices that are each in selective communication with the peer-to-peer server network.

4. The live-feed video balancing system of claim 3, wherein the customer terminal is one of a plurality of customer terminals that are each in selective communication with the peer-to-peer server network.

5. The live-feed video balancing system of claim 1, wherein the at least one corresponding performance criteria includes remaining data capacity.

6. The live-feed video balancing system of claim 2, wherein when one of the self-monitoring servers of the plurality of servers defines a failure mode characterized by absence of a communication to the remaining servers regarding the corresponding hosting capacity of the corresponding dedicated server, the remaining servers of the peer-to-peer server network that are free of the failure mode define a reallocated peer-to-peer server network, wherein the self-monitoring server that defines the failure mode is placed out of communication with the remaining servers of the reallocated peer-to-peer server network and also out of communication with the customer terminal and the image capturing device.

7. The live-feed video balancing system of claim 6, wherein when one of the self-monitoring servers defines the failure mode, the self-monitoring servers of the reallocated peer-to-peer server network communicate a failure signal to a service module corresponding to the self-monitoring server defining the failure mode.

8. The live-feed video balancing system of claim 1, wherein the plurality of servers are positioned within at least two separate physical locations.

9. A method for live streaming a plurality of server-hosted video feeds, the method comprising steps of:
   identifying a plurality of potential customer terminals;
   identifying a plurality of image capturing devices;

coupling a plurality of servers to define a peer-to-peer server network, wherein each server of the peer-to-peer server network is in communication with each remaining server of the peer-to-peer server network;

determining a corresponding hosting capacity for each server of the plurality of servers, wherein each server defines a monitoring server that operates to monitor at least one performance criteria of one corresponding monitored server within the peer-to-peer server network, wherein each monitoring server assigns a corresponding hosting capacity for the corresponding monitored server based upon the at least one performance criteria of the corresponding monitored server, and wherein the corresponding hosting capacity of each corresponding monitored server of the peer-to-peer server network is communicated to each remaining server of the peer-to-peer server network;

delivering a video request from a requesting customer terminal of the plurality of potential customer terminals to the peer-to-peer server network, wherein the video request identifies a requested image capturing device of the plurality of image capturing devices that is to be placed in communication with the requesting customer terminal via a hosting server of the peer-to-peer server network;

identifying the hosting server, wherein the hosting server is defined as the server having a first corresponding hosting capacity and the remaining servers are defined as having a range of second corresponding hosting capacities, wherein the first corresponding hosting capacity is greater than any of the corresponding hosting capacities within the range of second corresponding hosting capacities; and placing the requested image capturing device in communication with the hosting server and placing the hosting server in communication with the requesting customer terminal to deliver a live video feed from the requested image capturing device to the requesting customer terminal.

10. The method of claim 9, wherein each monitoring server is also the corresponding monitored server such that each server defines a self-monitoring server of the peer-to-peer server network that self-monitors the at least one performance criteria and communicates the at least one performance criteria to the remaining servers of the peer-to-peer server network.

11. The method of claim 9, wherein the step of determining a hosting capacity occurs substantially continuously.

12. The method of claim 9, wherein the step of determining a hosting capacity occurs at least after each video request is delivered.

13. The method of claim 10, wherein when one of the self-monitoring servers defines the hosting server with respect to at least one requested image capturing device and also defines a failure mode characterized by at least one of an absence of an outgoing communication to the remaining servers regarding the corresponding hosting capacity, the method further comprises the step of:

redefining the hosting server from the self-monitoring server that defines the failure mode to a self-monitoring server that is free of the failure mode and also defines the first corresponding hosting capacity.

14. The method of claim 13, wherein the method further comprises a step of:

the remaining servers communicating a failure signal to a service module corresponding the self-monitoring server defining the failure mode.

15. The method of claim 13, wherein the redefining step is performed by the self-monitoring servers of the peer-to-peer server network that are free of the failure mode.

16. The method of claim 9, wherein the at least one corresponding performance criteria includes a percentage of memory utilization.

17. A method for live streaming a plurality of server-hosted video feeds, the method comprising steps of:

defining a server web defined by a plurality of self-monitoring servers, wherein each self-monitoring server of the server web is in communication with each remaining server of the server web, and wherein each self-monitoring server monitors at least one corresponding performance criteria of the respective self-monitoring server, and wherein each self-monitoring server communicates the corresponding performance criteria to each remaining server of the server web;

determining a potential hosting server, wherein the self-monitoring servers of the server web assess each corresponding performance criteria to define a first performance criteria that corresponds to the potential hosting server, and wherein each remaining performance criteria of the remaining self-monitoring servers collectively defines a range of second performance criteria;

identifying a plurality of potential customer terminals;
identifying a plurality of image capturing devices;
delivering a video request from a requesting customer terminal of the plurality of potential customer terminals to the server web, wherein the video request identifies a requested image capturing device of the plurality of image capturing devices that is to be placed in communication with the requesting customer terminal via a hosting server of the peer-to-peer server network;

placing the potential hosting server in communication with the requested image capturing device and the requesting customer terminal, wherein the potential hosting server defines an active hosting server that places the requested image capturing device in communication with the requesting customer terminal via the active hosting server; and redetermining an updated potential hosting server wherein the active hosting server and the remaining self-monitoring servers of the server web communicates updated corresponding performance criteria to each other self-monitoring server of the server web to redefine an updated first corresponding performance criteria and an updated range of second corresponding performance criteria.

18. The method of claim 17, wherein the server web defines a peer-to-peer server network.

19. The method of claim 17, further comprising steps of:

receiving a video termination request from the requesting customer terminal that is in communication with the requested image capturing device via the active hosting server, wherein the termination request relates to selectively terminating the communication between the requesting customer terminal and the requested image capturing device;

stopping the live server-hosted video feed;

redetermining the corresponding performance criteria for each self-monitoring server in the server web; and redetermining the updated potential hosting server wherein the active hosting server and the remaining self-monitoring servers of the server web communicates updated corresponding performance criteria to each other self-monitoring server of the server web to redefine an updated first corresponding performance criteria and an updated range of second corresponding performance criteria.

20. The method of claim 17, wherein when one of the self-monitoring servers defines the active hosting server with respect to at least one requested image capturing device and also defines a failure mode characterized by at least one of an absence of an outgoing communication to the remaining self-monitoring servers regarding the corresponding performance criteria, the method further comprising a step of:

redefining the active hosting server from the self-monitoring server that defines the failure mode to a self-monitoring server that is free of the failure mode and also defines the first corresponding performance criteria.

* * * * *